US009011524B2

(12) United States Patent
Eberhardt (10) Patent No.: US 9,011,524 B2
(45) Date of Patent: Apr. 21, 2015

(54) PROSTHETIC HEART VALVES AND METHODS OF ATTACHING SAME

(75) Inventor: Carol E. Eberhardt, Fullerton, CA (US)

(73) Assignee: Medtronic, Inc., Minneapolis, MN (US)

( * ) Notice: Subject to any disclaimer, the term of this patent is extended or adjusted under 35 U.S.C. 154(b) by 347 days.

(21) Appl. No.: 12/766,554

(22) Filed: Apr. 23, 2010

(65) Prior Publication Data

US 2010/0274354 A1 Oct. 28, 2010

Related U.S. Application Data (60) Provisional application No. 61/214,590, filed on Apr. 24, 2009.

(51) Int. Cl.
| A61F 2/24 | (2006.01) |
| A61L 27/36 | (2006.01) |
| A61F 2/06 | (2013.01) |
| A61F 2/07 | (2013.01) |

(52) U.S. Cl.
CPC .......... *A61F 2/2412* (2013.01); *A61L 27/3625* (2013.01); *A61F 2250/0048* (2013.01); *A61F 2/064* (2013.01); *A61F 2002/075* (2013.01); *A61F 2250/0018* (2013.01); *A61F 2250/0037* (2013.01); *A61F 2250/0039* (2013.01); *A61F 2/07* (2013.01); *A61F 2/2418* (2013.01); *A61F 2220/0075* (2013.01); *A61F 2220/0008* (2013.01)

(58) Field of Classification Search
None
See application file for complete search history.

(56) References Cited

U.S. PATENT DOCUMENTS

| 3,671,979 | A | 6/1972 | Moulopoulos | |
| 4,056,854 | A | 11/1977 | Boretos et al. | |
| 4,994,077 | A | 2/1991 | Dobben | |
| 5,332,402 | A | 7/1994 | Teitelbaum | |
| 5,370,685 | A | 12/1994 | Stevens | |
| 5,397,351 | A | 3/1995 | Pavcnik et al. | |
| 5,554,185 | A | 9/1996 | Block et al. | |
| 5,855,601 | A | 1/1999 | Bessler et al. | |
| 6,168,614 | B1 | 1/2001 | Andersen et al. | |
| 6,206,931 | B1* | 3/2001 | Cook et al. | 623/23.75 |
| 6,669,724 | B2* | 12/2003 | Park et al. | 623/1.24 |
| 7,247,167 | B2* | 7/2007 | Gabbay | 623/2.14 |
| 2003/0014104 | A1* | 1/2003 | Cribier | 623/2.11 |
| 2003/0149477 | A1* | 8/2003 | Gabbay | 623/2.14 |
| 2004/0034411 | A1 | 2/2004 | Quijano et al. | |
| 2004/0206363 | A1* | 10/2004 | McCarthy et al. | 128/898 |
| 2004/0225353 | A1* | 11/2004 | McGuckin et al. | 623/2.11 |

(Continued)

OTHER PUBLICATIONS

Andersen, H.R. et al, "Transluminal implantation of artificial heart valves. Description of a new expandable aortic valve and initial results with implantation by catheter technique in closed chest pigs." Euro. Heart J. (1992) 13:704-708.

(Continued)

*Primary Examiner* — Thomas J Sweet
*Assistant Examiner* — Rebecca Preston (57) ABSTRACT

A stented valve including a compressible and expandable stent frame having a generally tubular body portion having an interior area and a longitudinal axis, a bioprosthetic valve positioned at least partially within the interior area of the tubular body portion of the stent frame and having an inner wall from which a plurality of leaflets extend; and a tubular covering material including a first portion extending from a first end of the stent frame to a second end of the stent frame, and a second portion extending beyond the second end of the stent frame.

15 Claims, 8 Drawing Sheets

(56) References Cited

U.S. PATENT DOCUMENTS

| | | | |
|---|---|---|---|
| 2005/0027348 A1* | 2/2005 | Case et al. | 623/1.24 |
| 2005/0137681 A1* | 6/2005 | Shoemaker et al. | 623/1.23 |
| 2009/0281609 A1* | 11/2009 | Benichou et al. | 623/1.11 |

OTHER PUBLICATIONS

Anderson, J. R., et al., "Transluminal Catheter Implantation of New Expandable Artificial Cardiac Valve", EUR Heart J., 1990, 11: (Suppl) 224a.

Block P C, "Clinical and Hemodyamic Follow-Up After Percutaneous Aortic Valvuloplasty in the Elderly", The American Journal of Cardiolo.y, vol. 62, Oct. 1, 1998.

Bonhoeffer, et al, "Percutaneous Insertion of the Pulmonary Valve," Journal of the American College of Cardiology (United States), May 15, 2002, pp. 1664-1669.

Bonhoeffer, P., "Transcatheter Implantation of a Bovine Valve in Pulmonary Position, a Lamb Study", Circulation, 2000:102:813-816.

Boudjemline, Y., "Percutaneous Implantation of a Valve in the Descending Aorta In Lambs", EUR Heart J, 2002; 23:1045-1049.

Boudjemline, et al, "Steps Toward Percutaneous Aortic Valve Replacement," Circulation (United States), Feb. 12, 2002, pp. 775-778.

Hilbert S. L., "Evaluation of Explanted Polyurethane Trileaflet Cardiac Valve Prosthesis", J Thorac Cardiovascular Surgery, 1989; 94:419-29.

Kulkinski, D., "Future Horizons in Surgical Aortic Valve Replacement: Lessons Learned During the Early Stages of Developing a Transluminal Implantation Technique", ASAIO J, 2004; 50:364-68.

* cited by examiner

PROSTHETIC HEART VALVES AND METHODS OF ATTACHING SAME

CROSS-REFERENCE TO RELATED APPLICATION

This application claims the benefit under 35 U.S.C. §119 (e) of U.S. Provisional Patent Application No. 61/214,590, filed Apr. 24, 2009, which is incorporated herein by reference in its entirety.

TECHNICAL FIELD

The present invention relates generally to prosthetic valves and more particularly relates to a surgical sutureless valve with an expandable sinus and anastomotic attachment.

BACKGROUND

Diseased or otherwise deficient heart valves can be repaired or replaced using a variety of different types of heart valve surgeries. Many heart valve surgeries involve an open-heart surgical procedure that is conducted under general anesthesia, during which the heart is stopped while blood flow is controlled by a heart-lung bypass machine. In some of these surgical procedures, it is necessary to remove portions of the native heart structure, such as the aorta, in order to restore proper functioning to a particular portion of the heart. In one example, after performing an aortotomy and removing the native aortic valve leaflets, a bioprosthesis is placed inside the native aorta and sewn into the patient's anatomy as a replacement for the aortic valve. In another example, a stented heart valve is sewn into place within patient's anatomy to replace an otherwise deficient valve. However, there is a desire to provide a replacement heart valve system that does not need to be sewn into place once it has been positioned properly relative to the anatomy of the patient in order to minimize the invasiveness of the procedure and minimize the time required to complete the surgical procedure.

BRIEF DESCRIPTION OF THE DRAWINGS

The present invention will be further explained with reference to the appended Figures, wherein like structure is referred to by like numerals throughout the several views, and wherein.

SUMMARY

In one embodiment of the invention, a stented valve is provided which includes a compressible and expandable stent frame having a generally tubular body portion having an interior area and a longitudinal axis, a bioprosthetic valve positioned at least partially within the interior area of the tubular body portion of the stent frame and having an inner wall from which a plurality of leaflets extend; and a tubular covering material including a first portion extending from a first end of the stent frame to a second end of the stent frame, and a second portion extending beyond the second end of the stent frame.

In another embodiment of the invention, a method is provided for implanting a stented valve comprising the steps of: providing a stented valve that includes a compressible and expandable stent frame having a generally tubular body portion having an interior area and a longitudinal axis, a bioprosthetic valve positioned at least partially within the interior area of the tubular body portion of the stent frame and having an inner wall from which a plurality of leaflets extend; and a tubular covering material including a first portion extending from a first end of the stent frame to a second end of the stent frame, and a second portion extending beyond the second end of the stent frame, then inserting the second portion of the tubular covering material into an aortic opening having an edge, wrapping the second portion of the tubular covering material over the edge of the aortic opening, and attaching an adjacent tubular structure to the second portion of the tubular covering material.

DETAILED DESCRIPTION

As referred to herein, the prosthetic heart valves used in accordance with various devices and methods of heart valve delivery may include a wide variety of different configurations, such as a prosthetic heart valve having tissue leaflets or a synthetic heart valve having polymeric, metallic, or tissue-engineered leaflets, and can be specifically configured for replacing any heart valve. In addition, while much of the description herein refers to replacement of aortic valves, the prosthetic heart valves and methods of the invention can also generally be used for replacement of native mitral, pulmonic, or tricuspid valves, for use as a venous valve, or to replace a failed bioprosthesis, such as in the area of an aortic valve or mitral valve, for example.

In general, the stent structures of the invention can include a number of strut or wire portions arranged relative to each other to provide a desired compressibility, strength, and leaflet attachment zone(s) to the heart valve. Other details on particular configurations of the stents of the invention are also described below; however, in general terms, stents of the invention are generally tubular support structures, and leaflets will be secured within each support structure to provide a stented valve. The leaflets can be formed from a variety of materials, such as autologous tissue, xenograph material, or synthetics, as are known in the art. The leaflets may be provided as a homogenous, biological valve structure, such as a porcine, bovine, or equine valve. Alternatively, the leaflets can be provided as independent structures (e.g., as can be formed with bovine or equine pericardial leaflets) and subsequently assembled to the support structure of the stent. In another alternative, the stent and leaflets can be fabricated at the same time, such as may be accomplished using high strength nano-manufactured NiTi films of the type produced at Advanced Bio Prosthetic Surfaces Ltd. (ABPS) of San Antonio, Tex., for example. The support structures are generally configured to accommodate three leaflets; however, the replacement prosthetic heart valves of the invention can incorporate more or less than three leaflets.

In more general terms, the combination of a support structure with one or more leaflets can assume a variety of other configurations that differ from those shown and described, including any known prosthetic heart valve design. In certain embodiments of the invention, the support structure with leaflets utilize certain features of known expandable prosthetic heart valve configurations, whether balloon expandable, self-expanding, or unfurling (as described, for example, in U.S. Pat. Nos. 3,671,979; 4,056,854; 4,994,077; 5,332,402; 5,370,685; 5,397,351; 5,554,185; 5,855,601; and 6,168,614; U.S. Patent Application Publication No. 2004/0034411; Bonhoeffer P., et al., "Percutaneous Insertion of the Pulmonary Valve", Pediatric Cardiology, 2002; 39:1664-1669; Anderson H R, et al., "Transluminal Implantation of Artificial Heart Valves", EUR Heart J., 1992; 13:704-708; Anderson, J. R., et al., "Transluminal Catheter Implantation of New Expandable Artificial Cardiac Valve", EUR Heart J., 1990, 11: (Suppl) 224a; Hilbert S. L., "Evaluation of Explanted Polyurethane Trileaflet Cardiac Valve Prosthesis", J Thorac Cardiovascular Surgery, 1989; 94:419-29; Block P C, "Clinical and Hemodyamic Follow-Up After Percutaneous Aortic Valvuloplasty in the Elderly", The American Journal of Cardiology, Vol. 62, Oct. 1, 1998; Boudjemline, Y., "Steps Toward Percutaneous Aortic Valve Replacement", Circulation, 2002; 105:775-558; Bonhoeffer, P., "Transcatheter Implantation of a Bovine Valve in Pulmonary Position, a Lamb Study", Circulation, 2000:102:813-816; Boudjemline, Y., "Percutaneous Implantation of a Valve in the Descending Aorta In Lambs", EUR Heart J, 2002; 23:1045-1049; Kulkinski, D., "Future Horizons in Surgical Aortic Valve Replacement: Lessons Learned During the Early Stages of Developing a Transluminal Implantation Technique", ASAIO J, 2004; 50:364-68; the teachings of which are all incorporated herein by reference).

The various support structures or stent frames described herein can be a series of wires or wire segments arranged so that they are capable of transitioning from a collapsed state or semi-collapsed state to an expanded state. In some embodiments, a number of individual wires comprising the support structure can be formed of a metal or other material. These wires are arranged in such a way that a support structure allows for folding or compressing to a contracted state in which its internal diameter is at least slightly reduced from its internal diameter in an expanded state. The wires of the stent frames can be formed from a shape memory material such as a nickel titanium alloy (e.g., Nitinol) or a very high-tensile material that will expand from its compressed state to its original state after removal of external forces.

With this material, the support structure is self-expandable from a contracted state to an expanded state, such as by the application of heat, energy, and the like, or by the removal of external forces (e.g., compressive forces). This support structure can be repeatedly compressed and re-expanded without damaging the structure of the stent. The support structure of such an embodiment may be laser cut from a single piece of material or may be assembled from a number of different components.

Figure 1:
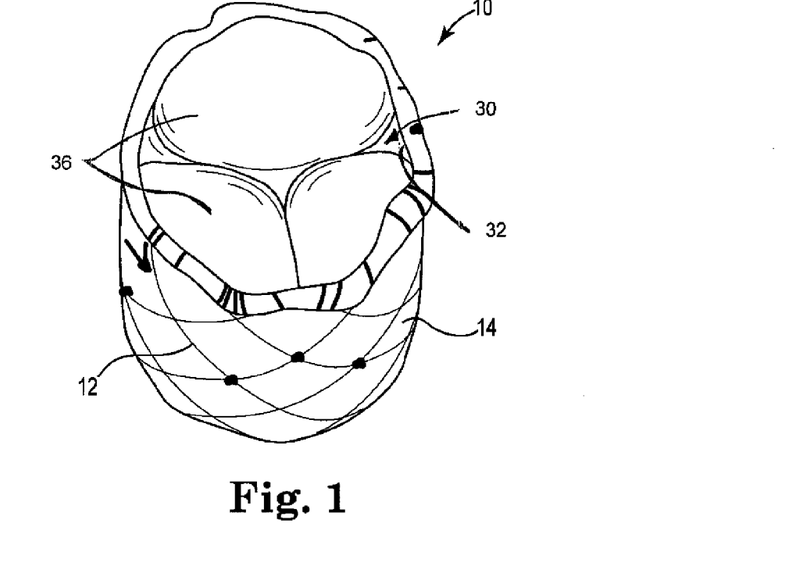
FIG. 1 is a top perspective view of an embodiment of a stented valve of the invention.
Figure 2:
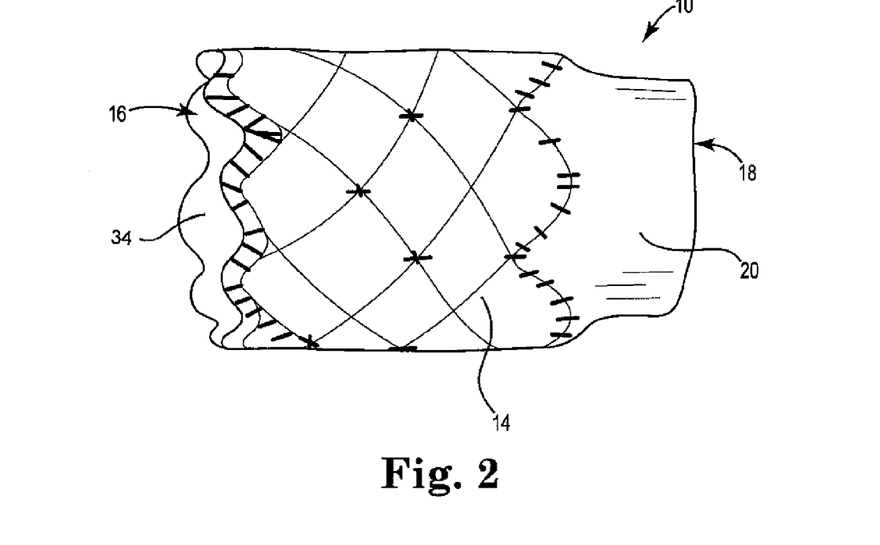
FIG. 2 is a side view of the stented valve of FIG. 1.
Figure 3:
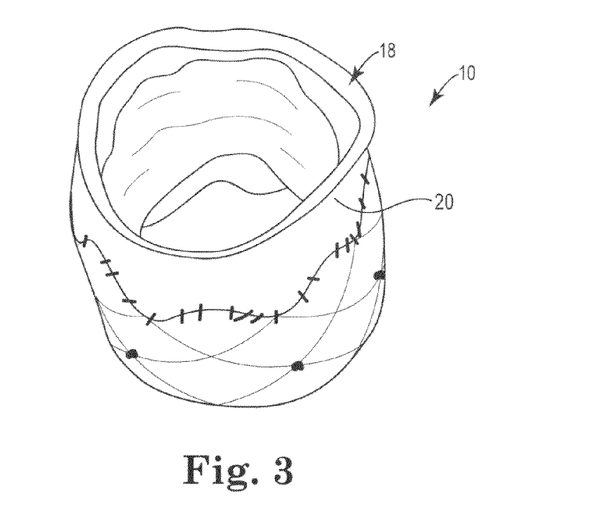
FIG. 3 is a bottom view of the stented valve of FIG. 1.

Referring now to the Figures, wherein the components are labeled with like numerals throughout the several Figures, and initially to FIGS. 1-10, an exemplary stented valve 10 and its implantation in a representative implantation site, in accordance with the invention, is illustrated. In particular, FIG. 1 illustrates a top view and FIG. 2 illustrates a front view of a stented valve that can be used in an anastomosis procedure. The stented valve comprises a stent frame 12 that can be compressible and expandable, if desired, and a covering material 14. The covering material may be tissue, such as pericardial tissue, cloth, or the like, or another biocompatible material. The stented valve 10 further includes a valve 30 positioned within an interior area of the stent frame 12. The valve 30 includes a tubular member 32 with an inner wall 34 from which a plurality of leaflets 36 extend into the internal area of the stented valve 10. The valve 30 is shown in a generally closed configuration in FIG. 1 and in a generally open configuration in FIG. 3. As is illustrated in many of the Figures, such as FIGS. 1-4, a portion of the covering material 14 is stitched to the stent frame 12 along both ends of the stent frame in a zigzag pattern. Additional stitches between the ends of the stent frame 12 can also optionally be used to provide additional points where the covering material 14 is secured to the stent frame 12, such as in the areas of the commissures, in a predetermined stitching pattern, or in random locations around the periphery of the covering material 14, for example. The stented valve 10 further includes a first end 16 that generally coincides with one end of the stent frame 12, and a second end 18. The second end 18 is adjacent to a portion of the covering material 14 that extends beyond the opposite end of the stent frame 12, which thereby provides a tubular, extending piece of covering material 20 that is not supported by the stent frame 12. For illustration purposes, a transcatheter pulmonary valve without sinus openings is shown; however, a number of different types of valves can instead be used, wherein a piece or section of tubing material extends beyond the edge of its stent frame, and wherein this section of material will be referred to herein as the "unsupported tubing material".

Figure 4:
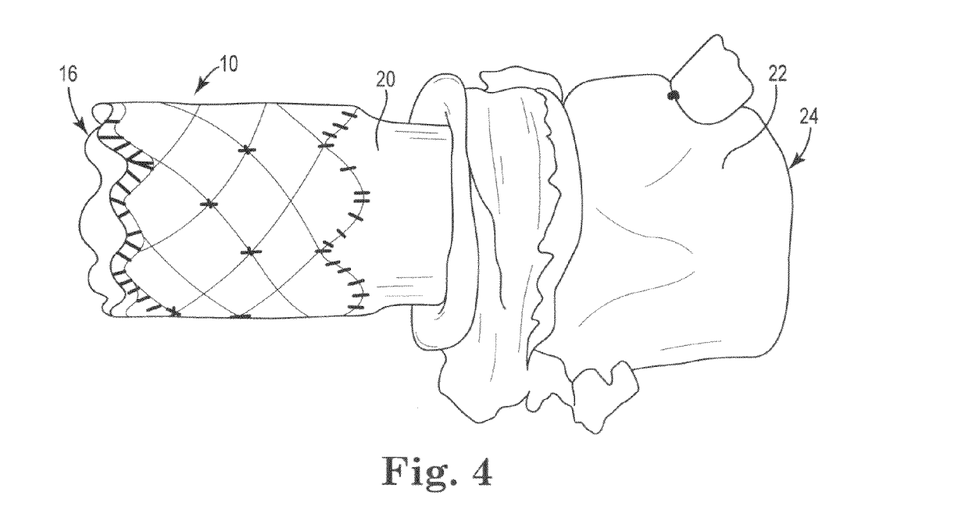
FIG. 4 is a side view of the stented valve of FIG. 1 being inserted into a representative implantation site.
Figure 5:
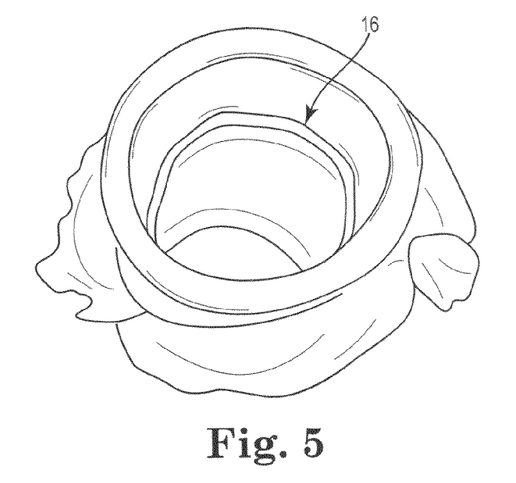
FIG. 5 is a top view of the stented valve of FIG. 1 inserted into the representative implantation site.
Figure 6:
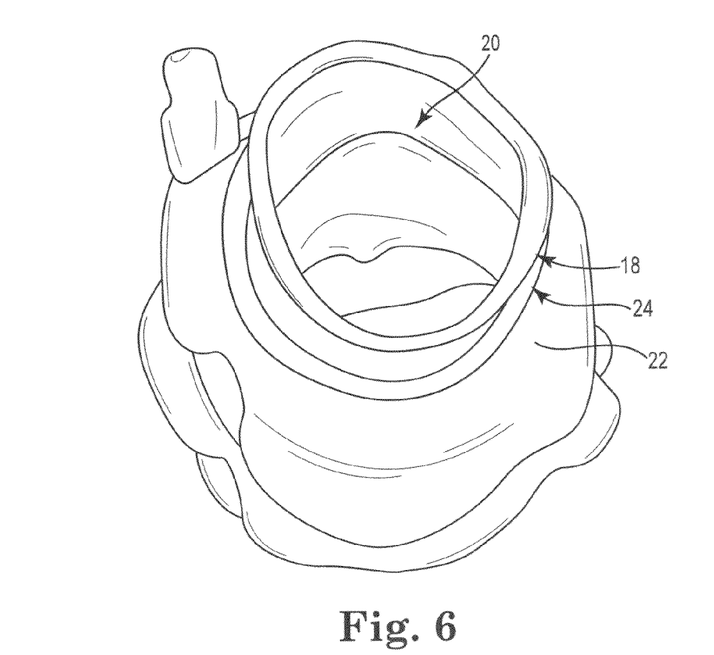
FIG. 6 is a bottom view of the implanted valve configuration of FIG. 5.
Figure 7:
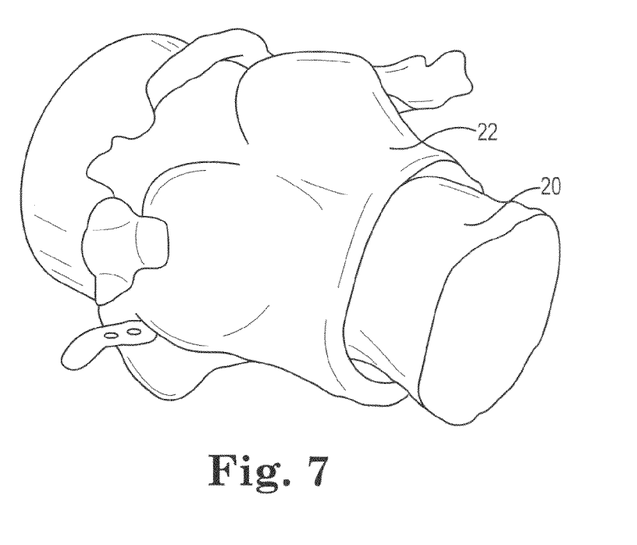
FIG. 7 is a side view of the implanted valve configuration of FIG. 5.

FIG. 4 illustrates the stented valve 10 described above positioned relative to a host valve implant site. For purposes of these illustrations, the host valve implant site is shown as a Freestyle valve 22 of the type commercially available from Medtronic, Inc., of Minneapolis, Minn. However, the implantation site may instead be a native vessel, such as a native aorta, for example, which is severed at an area adjacent to the native leaflets. With particular reference to FIGS. 4-7, the second end 18 of the stented valve 10 described above is inserted into the host valve implant site, such as an aorta or Freestyle valve 22, with the unsupported tubing material 20 being inserted until it extends beyond an edge of the aorta that has previously been cut in a surgical procedure (as is illustrated with an end 24 of the Freestyle valve 22 and as is illustrated in FIGS. 6 and 7). In order to facilitate the process of inserting this stented valve 10 into the opening at the implantation site, the stented valve 10 can be compressed at least slightly, if desired. At any point during this procedure that is determined to be appropriate by the surgeon, the stent frame 12 can be released and allowed to expand so that its outward bias (provided by the shape memory material) will hold it in place at its desired location. In one method of the invention, at least a portion of the length of the unsupported tubing material 20 will extend beyond the cut edge of the aorta, as is illustrated in FIGS. 5-7, and the remainder of the stented valve 10 will be properly positioned within the vessel. The unsupported tubing material 20 can then be trimmed, if desired, depending on the length that the aorta was trimmed.

Figure 8:
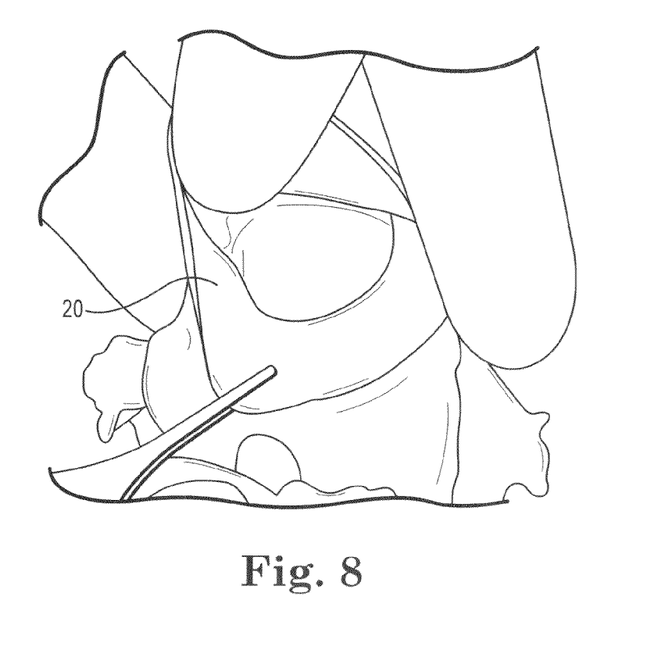
FIG. 8 is a perspective view of the implanted valve configuration of FIG. 5, with an unsupported tube portion being wrapped over an edge of the representative implantation site.
Figure 9:
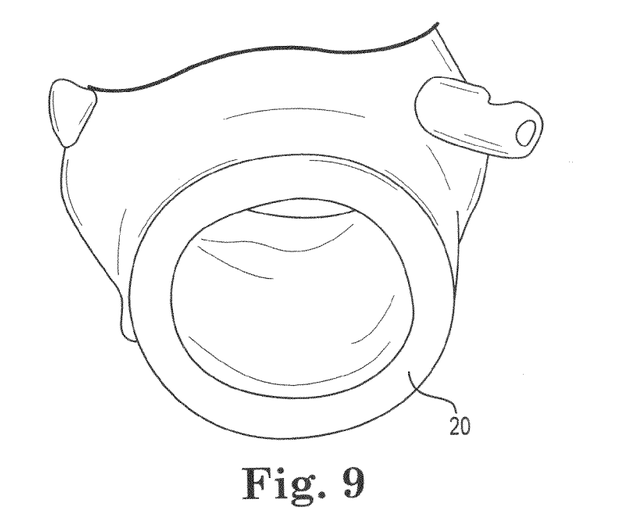
FIG. 9 is a perspective view of the implanted valve configuration of FIG. 8 after the tube portion is wrapped over the edge of the representative implantation site.
Figure 10:
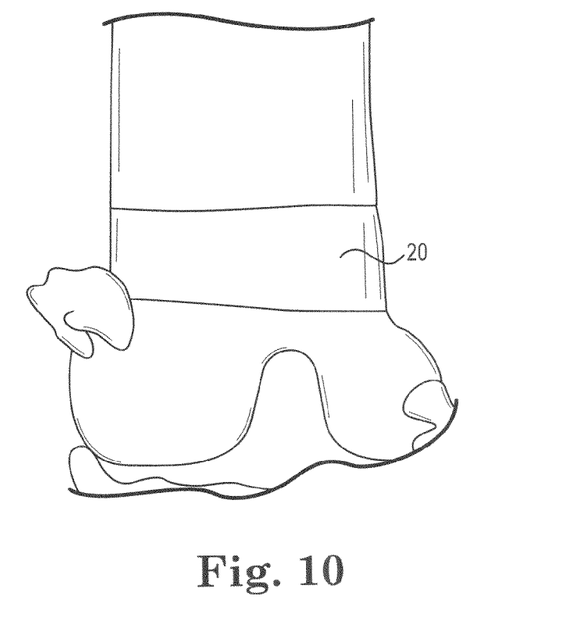
FIG. 10 is a front view of the valve arrangement of FIG. 9 relative to a representative aorta.

The remaining unsupported tubing material 20 is then wrapped over the trimmed edge of the aorta, as is illustrated in FIG. 8, which will result in an edge that resembles that shown in FIG. 9. This material 20 can then be sewn through the tube and to the cut end of the native aorta, with the components in the general arrangement illustrated in FIG. 10. That is, the unsupported tubing material 20, which has been wrapped over one trimmed edge of the aorta, is used for attaching into the anastomosis by stitching or other attachment methods.

Figure 11:
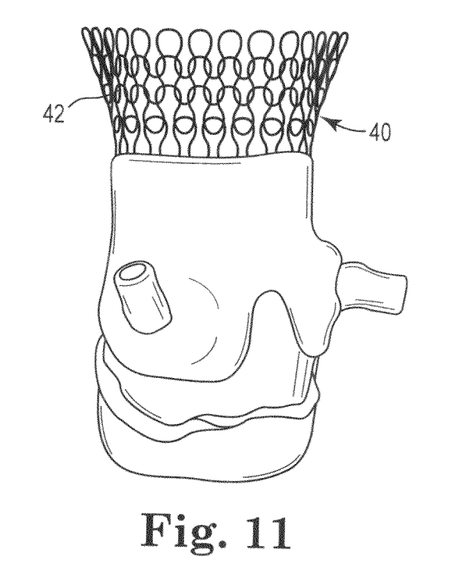
FIG. 11 is a front view of a mesh stent extending past a representative edge of an aorta.
Figure 12:
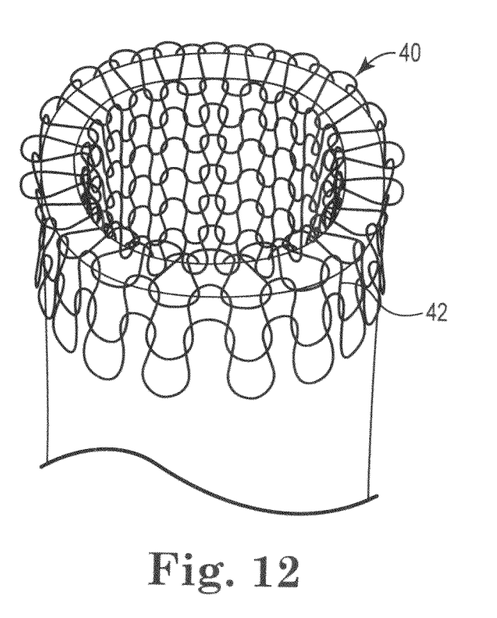
FIG. 12 is a top perspective view of a mesh stent folded over the representative edge of the aorta of FIG. 11.
Figure 13:
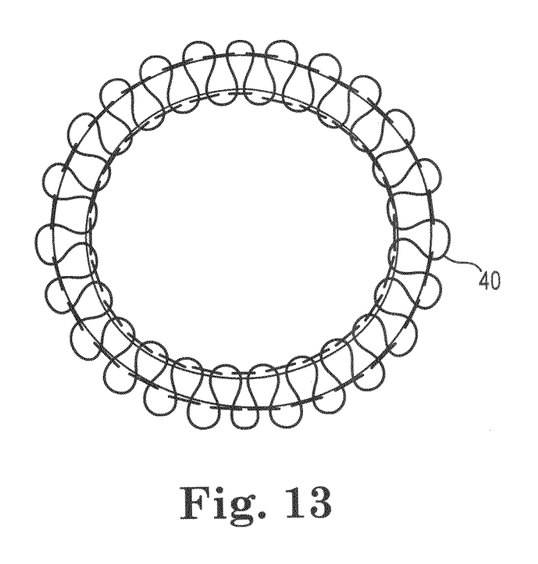
FIG. 13 is a top view of the mesh stent within the representative aorta illustrated in FIG. 12.

FIGS. 11-13 illustrate an alternative arrangement of stent placement that includes inserting a mesh stent structure 40 of the type illustrated in FIG. 11 into a vessel, such as an aorta, so that a free end or unsupported portion 42 extends beyond the free or trimmed end of the vessel. The mesh stent structure 40 can be made of a shape memory material such as Nitinol, for example, or another material that is not a shape memory material. This portion 42 of the mesh stent structure 40 is then wrapped over the trimmed edge of the aorta so that it is positioned on the outside of the aorta. The portion 42 may then be used for attachment to a free edge of an adjacent vessel, such as in an anastomosis procedure, for example.

Figure 14:
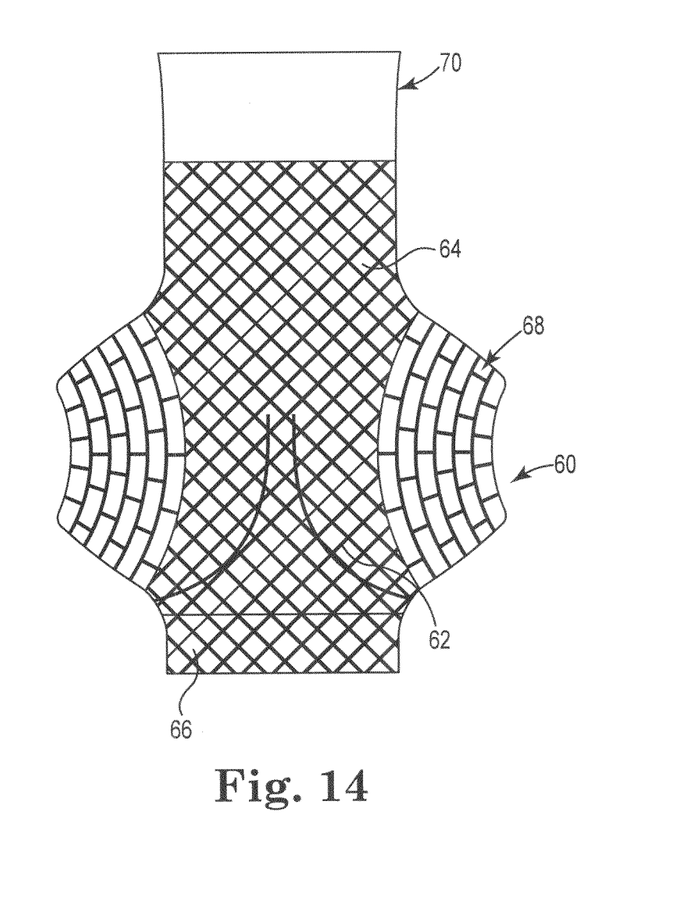
FIG. 14 is a front view of an embodiment of a valve with an expanding sinus portion.

FIG. 14 illustrates another embodiment of a surgical valve 60 of the invention. Surgical valve 60 includes a stent 62 and a covering 64. The stent 62 includes an expandable annular section 66, an expandable sinus area 68, and an outflow section 70 including a tube of either cloth, tissue, or the stent itself sewn into the anastomosis for securing the outflow section. The tube 70 is attached to the expandable stent 62 either on the inside, the outside, or both the inside and outside of the stent. The tube section 70 extends beyond the stent frame 62 and is then trimmed to the length needed for the anastomosis. The process could alternatively be performed with just the stent in the case of a stent material that can be trimmed. The trimmed tube section can then be included in the anastomosis by several methods, which may include either folding the tube over the end of the aorta and sewing it into the anastomosis site, and/or tack-stitching on the inside to hold the device in place while sewing it into the anastomosis site.

The expandable sinus area 68 of this device of FIG. 14 can include multiple ring sections that allow expansion into variable geometries of the sinus. Expansion of the sinus rings will secure the device in place and the "functional" valve section will not expand, thereby ensuring competence of the valve leaflets. The annular section 66 will extend below the leaflets so that it can expand out into the valve annulus. This section can be covered with tissue, cloth, or the like, if desired, or it can remain uncovered, as shown. Thus, this device is provided with an expanding sinus having coronary openings that expand to accommodate various sinus shapes and sizes. The section holding the valves preferably does not expand, although it can be at least slightly compressible and expandable, if desired. The outflow stent section 70 can be stitched into the anastomosis site by attaching a tube to the stent that can be trimmed to length and then sutured into the anastomosis site, for example.

The present invention has now been described with reference to several embodiments thereof. The contents of any patents or patent application cited herein are incorporated by reference in their entireties. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

What is claimed is:

1. A stented valve suitable for implantation within a patient, the stented valve extending between, and terminating at, opposing first and second terminal ends, the stented valve comprising:
   a compressible and expandable stent frame comprising a generally tubular body portion having an interior area and a longitudinal axis;
   a prosthetic heart valve positioned within the interior area of the tubular body portion of the stent frame and provided as a homogeneous, biological valve structure comprising an inner wall from which a plurality of leaflets extend, the prosthetic heart valve selected from the group consisting of a porcine valve, a bovine valve, and an equine valve; and
   a tubular covering material comprising a first portion on an outside of the stent frame and extending from a first end of the stent frame to a second end of the stent frame, the tubular covering material securely stitched to the first end and the second end, the first end of the stent frame coinciding with the first terminal end, and a second portion of the tubular covering material extending beyond the second end of the stent frame to the second terminal end, wherein an end of the first portion of the tubular covering material is attached to the second end of the stent frame, and wherein an entirety of the second portion comprises a single layer of unsupported tubular covering material configured for anastomotic attachment, the second portion defining a continuous, uninterrupted, closed perimeter shape in a plane perpendicular to the longitudinal axis beyond the second end of the stent frame and the prosthetic heart valve.

2. The stented valve of claim 1, wherein the tubular covering material comprises pericardial material.

3. The stented valve of claim 1, wherein the stent frame comprises a shape memory material.

4. The stented valve of claim 1, wherein stitches at the first end of the stent frame form a proximal attachment pattern along which the first portion of the tubular covering material is attached to the first end of the stent frame.

5. The stented valve of claim 4, wherein the proximal attachment pattern comprises a zigzag pattern.

6. The stented valve of claim 5, wherein the proximal attachment pattern generally follows wire segments that define the first end of the stent frame.

7. The stented valve of claim 1, wherein stitches at the second end of the stent frame form a distal attachment pattern along which the first portion of the tubular covering material is attached to the second end of the stent frame and from which the second portion of the tubular covering material extends.

8. The stented valve of claim 7, wherein the distal attachment pattern comprises a zigzag pattern.

9. The stented valve of claim 8, wherein the distal attachment pattern generally follows wire segments that define the second end of the stent frame.

10. The stented valve of claim 1, wherein the plurality of leaflets comprises three leaflets.

11. The stented valve of claim 1, wherein the plurality of leaflets are formed from pericardial tissue.

12. The stented valve of claim 1, wherein the plurality of leaflets are formed from porcine, bovine or equine tissue.

13. The stented valve of claim 1, wherein the leaflets are formed from porcine, bovine or equine pericardial tissue.

14. The stented valve of claim 1, wherein the plurality of leaflets are provided as a biological valve structure derived from a pig, cow or horse.

15. The stented valve of claim 1, wherein an outer diameter defined by the stent frame is greater than an outer diameter defined by the second portion of the tubular covering material in a normal state of the stented valve.

\* \* \* \* \*